United States Patent
Watson

(10) Patent No.: US 10,162,029 B2
(45) Date of Patent: Dec. 25, 2018

(54) MAGNETIC LENSING FOR BETA EMISSION IMAGING

(71) Applicant: Siemens Medical Solutions USA, Inc., Malvern, PA (US)

(72) Inventor: Charles C. Watson, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 15/980,777

(22) Filed: May 16, 2018

(65) Prior Publication Data

US 2018/0267121 A1 Sep. 20, 2018

Related U.S. Application Data

(62) Division of application No. 15/641,449, filed on Jul. 5, 2017, now Pat. No. 10,018,696.

(60) Provisional application No. 62/360,598, filed on Jul. 11, 2016.

(51) Int. Cl.
*G01T 1/29* (2006.01)
*G01R 33/48* (2006.01)
*G01N 33/483* (2006.01)

(52) U.S. Cl.
CPC ....... *G01R 33/481* (2013.01); *G01N 33/4833* (2013.01); *G01T 1/2985* (2013.01)

(58) Field of Classification Search
CPC . G01N 33/4833; G01R 33/481; G01T 1/2985
See application file for complete search history.

(56) References Cited

U.S. PATENT DOCUMENTS

| 2011/0224534 A1* | 9/2011 | Yamaya | G01R 33/481 600/411 |
|---|---|---|---|
| 2012/0018643 A1 | 1/2012 | Caruba et al. | |
| 2014/0228673 A1 | 8/2014 | Watson | |
| 2015/0045653 A1 | 2/2015 | Okamoto et al. | |
| 2016/0116614 A1 | 4/2016 | Watson | |

OTHER PUBLICATIONS

Iida, H., et al. "A simulation study of a method to reduce positron annihilation spread distributions using a strong magnetic field in positron emission tomography." IEEE Transactions on Nuclear Science 33.1 (1986): 597-600.
Watson, Charles C. "Imaging the attenuation coefficients of magnetically constrained positron beams in matter." Nuclear Instruments and Methods in Physics Research Section B: Beam Interactions with Materials and Atoms 383 (2016): 234-244.

* cited by examiner

*Primary Examiner* — Eliza Osenbaugh-Stewart

(57) ABSTRACT

In beta emission imaging, magnetic lensing allows a lower resolution detector to detect the spatial distribution of emissions at a higher resolution. The sample is placed in a magnetic field with field lines at a given density, and the detector is placed away from the sample where the magnet field lines diverge, resulting in a lesser density. Since the beta emissions travel along the field lines, the divergence of the field lines from the sample to the detector result in lensing or magnification. Using positron attenuation tomography to detect annihilation in the detector allows for correction due to self-absorption by the sample. The correction and lensing are used together or may be used independently.

7 Claims, 4 Drawing Sheets

MAGNETIC LENSING FOR BETA EMISSION IMAGING

RELATED APPLICATIONS

The present patent document is a divisional application of U.S. patent application Ser. No. 15/641,449, filed Jul. 5, 2017, which claims the benefit of the filing date under 35 U.S.C. § 119(e) of Provisional U.S. Patent Application Ser. No. 62/360,598, filed Jul. 11, 2016, both of which are hereby incorporated by reference.

BACKGROUND

The present embodiments relate to beta emission imaging. Beta ray emission imaging is used to study the distribution of labeled biological tracers in plant tissues, animal tissues, or other tissue samples.

Beta emission imaging has several limitations. The spatial resolution, and resulting utility, of beta emission imaging is limited by the detector. The tissue of the sample may be thicker in some places than others or include materials that attenuate the beta emissions differently prior to reaching the detector. This variable attenuation or self-absorption may cause errors in the interpretation of the detected intensity or counts.

Improving spatial resolution has primarily been addressed by constructing beta detectors with higher density readout capabilities. This approach has technological limitations. It is further limited by the isotropic emission of beta rays and their finite range in matter (e.g., on the order of 1 mm or greater at 1 $g/cm^3$), particularly if higher energy betas are used to see through thicker layers of tissue.

SUMMARY

By way of introduction, the preferred embodiments described below provide systems, methods, and computer readable media for beta emission imaging. Magnetic lensing allows a lower resolution detector to detect the spatial distribution of emissions at a higher resolution. The sample is placed in a magnetic field with field lines at a given density, and the detector is placed away from the sample where the magnet field lines diverge, resulting in a lesser density. Since the beta emissions travel along the field lines, the divergence of the field lines from the sample to the detector results in lensing or magnification. Using positron attenuation tomography to detect annihilation in the detector allows for correction due to self-absorption by the sample. The correction and lensing are used together or may be used independently.

In a first aspect, a beta emission imaging system is provided. A magnet is operable to generate a magnetic field through an object. The magnet has ends beyond which magnetic field lines of the magnetic field diverge. A positron absorber is positioned beyond one of the ends of the magnet where the magnetic field lines of the magnetic field diverge. A positron emission tomography system is configured to detect annihilation events in the positron absorber. The annihilation events are from beta emissions from the object between the ends of the magnet. The positron emission tomography system is configured to reconstruct a spatial distribution of the beta emissions in the object. A display is configured to display an image of the spatial distribution.

In a second aspect, a method is provided for magnetic lensing in beta emission imaging. Beta emissions are generated from a sample positioned in magnetic field lines having a first density. The beta emissions are detected at a location spaced from the sample where the magnetic field lines have a second density, less than the first density. An image of the detected beta emissions of the sample is formed.

In a third aspect, a method is provided for beta emission imaging. Values for a spatial distribution of beta emissions from biological object are detected. Attenuation of the beta emissions is determined. The determination is of the attenuation of the beta rays within the biological object. The values for the beta emissions are corrected with the attenuation. An image of the spatial distribution of the beta emissions from the biological object is generated with the values as corrected.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Magnetic lensing may improve the resolution of beta emission imaging. The spatial resolution of beta emission images is improvided without a corresponding increase in physical resolution of the detector. The beta emission imaging is performed with a diverging magnetic field to guide beta rays emerging from a sample to a detector while spreading the rays spatially like a magnifying lens. The spatial resolution of the emission distribution is improved.

The beta emission image may be corrected for self-absorption within the sample being imaged. A positron attenuation tomography (PAT) system is used to measure the emitted flux distribution at the detector or positron absorber. The flux distribution is used to correct for self-absorption in the sample. The confounding effect of variable self-attenuation in the sample is reduced.

Figure 3:
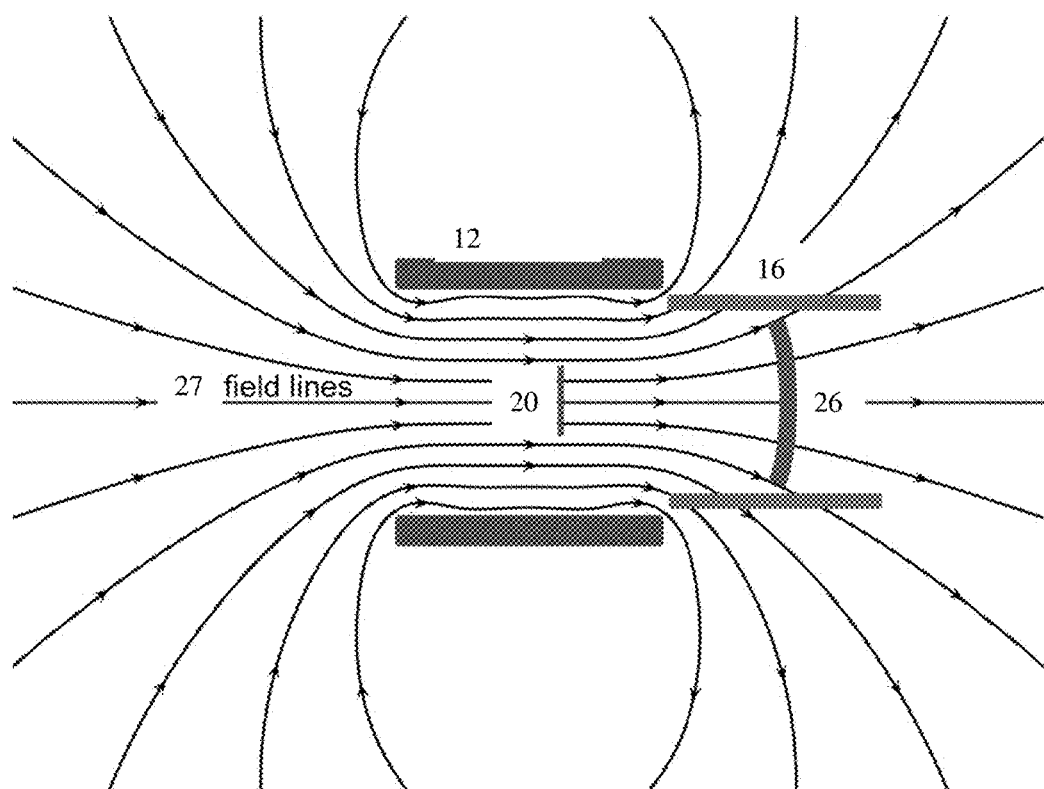
FIG. 3 shows magnetic field lines for beta emission imaging with magnetic lensing.
Figure 5:
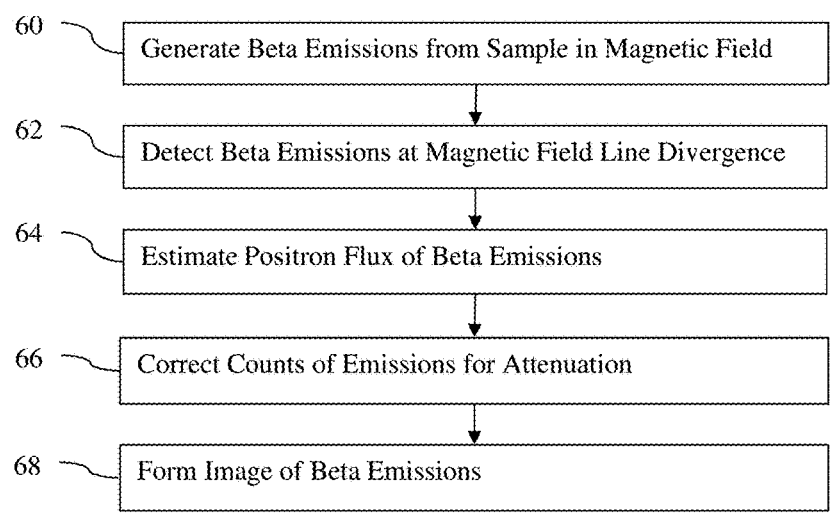
FIG. 5 is a flow chart diagram of an example embodiment of a method for beta emission imaging.

The magnetic lensing and correction for self-absorption may be used together or independently. One beta emission imaging embodiment may include just the magnetic lensing, and another beta emission imaging embodiment may include just the correction for self-absorption. Since both the correction with PAT and the magnetic lensing rely on beta emission imaging under the influence of a magnetic field, both may be used together in one embodiment. The embodiments of FIGS. 1, 3, and 5 are directed to the combination, but may be used for only either one of the two.

Figure 1:
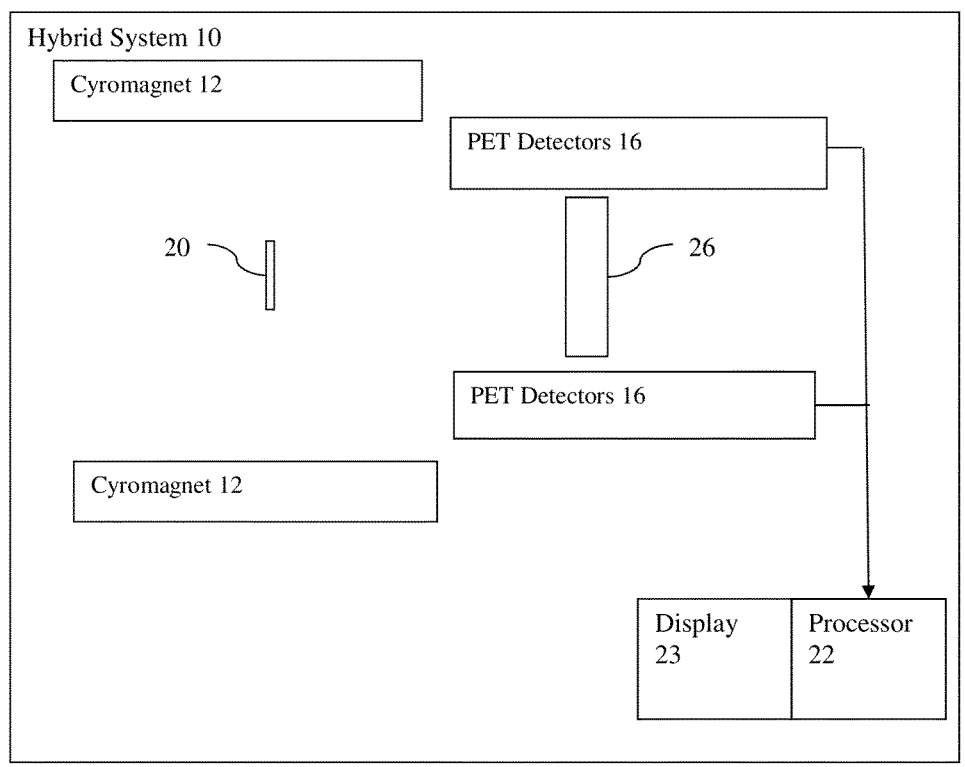
FIG. 1 is a block diagram of one embodiment of a hybrid PET/MR system for beta emission imaging.

FIG. 1 shows a beta emission imaging system. Magnetic lensing and/or correction for self-absorption are used in beta emission imaging. The beta emission system uses a hybrid magnetic resonance (MR) and positron emission tomography (PET) system 10. The hybrid PET/MR system 10 shown includes PET and MR portions. The PET and MR portions other than the processor 22 and display 24 are integrated into one device or within a common housing. The parts of the hybrid system 10 shown in FIG. 1 are in a single freestanding unit. The PET portion is shown extending from, removed from, or in a service position where the PET detectors 16 extend beyond the bore of the magnet 12. In other embodiments, components of the hybrid PET/MR system 10 shown in FIG. 1 are in separate housings or separate freestanding units. The processor 22 communicates with data acquisition units of the PET portion through a filter plate for routing communications and power through the RF cabin for housing the MR portion.

Figure 2:
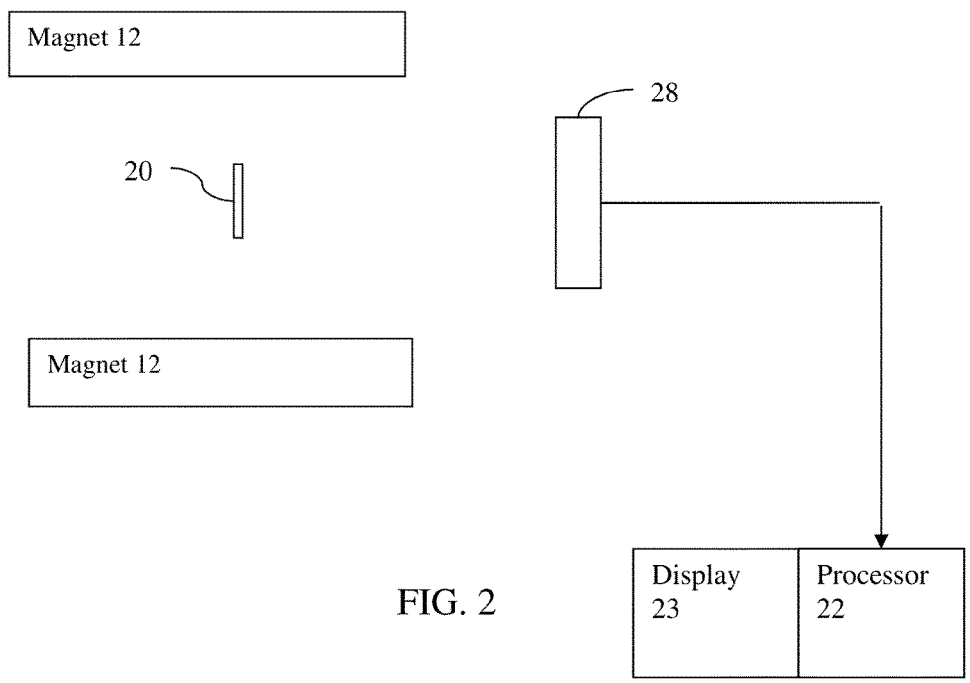
FIG. 2 is a block diagram of one embodiment of a beta emission imaging system using direct beta emission detection.

Only parts of the PET portion and parts of the MR portion are shown. Additional, different, or fewer components may be provided. In other embodiments, the PET system does not include the MR imager, but instead uses another source of magnetic fields. In yet other embodiments, the MR portion does not include the PET system, but instead includes a detector for detecting beta emissions. FIG. 2 shows one embodiment of a beta emission imaging system using magnetic lensing. The magnet 12 is provided for use with a beta emission detector 28 without the PET portion.

In FIGS. 1 and 2, the magnet generates a magnetic field. Any magnet may be used, such as a cryomagnet or another main magnet of a MR device or a Helmholtz coil. For example, the main field (i.e., $B_0$) magnet of a MR imager is used. The magnet 12 is one or more tesla in strength, such as being 3T or 9T. The cryomagnet 12 generates a strong static main magnetic field $B_0$ in the range of, for example, 1 Tesla to 3 Tesla or more.

The magnet 12 is a cylinder, but may have other shapes. A plurality of separate magnets may be used to form the magnetic field. A bar or another shaped single magnet may be used. As a cylinder or other shape with a hollow center, the magnet 12 forms a bore. A tubular or laterally open examination region of the magnet forms the bore.

The main magnetic field $B_0$ is approximately homogeneous in the bore of the magnet 12. The main magnetic field $B_0$ extends throughout the RF cabin along magnetic field lines 27, as represented in FIG. 3. Different regions within the RF cabin may be subjected to stronger or weaker magnetic fields. For example, the ends of the cryomagnet 12 may have weaker magnetic field strength.

The magnet 12 includes two ends, such as at the outer extent of the bore. The ends or other extent of the magnet 12 define a region within the bore having a generally uniform (e.g., generally is less than 0.1% deviation) density of parallel magnetic field lines 27. At the ends and beyond the ends, the magnetic field lines 27 diverge from each other.

The magnet 12 has any orientation or position relative to the object 20 being examined. Any object 20 may be used, such as a biological sample. Plant, animal, or other tissue sample may be injected with a radio-tracer. The radio-tracer migrates to or attaches to tissue or material, such as associated with uptake or other biological function. In one example, the sample is a leaf. The radio-tracer attaches to carbon for imaging carbon migration.

The object 20 is positioned in the main field. The object 20 is positioned in the bore, so is subjected to the substantially uniform region of the magnetic field lines 27. Other positions, such as at the ends of the bore, may be used. The magnet 12 generates magnetic field lines through the object 20.

The radio-tracer includes a radioactive emitter. For example, $^{68}$Ga, $^{18}$F, or $^{11}$C are used. Due to decay, the radioactive emitter emits beta particles. Positrons or electrons are emitted. For use with a PET system, positron emitters are used. The beta emissions will travel in either direction along the magnetic field lines 27. The magnet 12 establishes uniform field lines 27 in the bore about which the beta particles emitted from the sample 20 travel in a helical path. As the field lines 27 diverge, the beta particles likewise diverge.

The MR portion of the hybrid system 10 is shown as the cryomagnet 12. Additional, different, or fewer components may be provided. For example, a platform for testing materials, a bed, a body coil, and/or gradient coils are provided. Other parts of the MR portion may be provided within a same housing, within a same room (e.g., within the radio frequency (RF) cabin), or within a same facility. The other parts of the MR portion may include local coils, cooling systems, pulse generation systems, image-processing systems, and user interface systems. The location of the different components of the MR portion is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate. In other embodiments, just the cryomagnet 12 is provided without the rest of the MR portion as MR imaging may not be used.

In the embodiments of FIGS. 1 and 3, a positron absorber 26 is provided. The positron absorber 26 is any material for stopping or interacting with the beta emissions (i.e., positrons). For attenuation detection, the material is less dense, such as a polyethylene foam block. Denser or less dense materials may be used. The positron absorber 26 is uniform, but may have varying density and/or material composition. The positron absorber 26 has any size and shape. FIG. 1 shows a rectangular cross-section of a plate or cuboid shape. FIG. 3 shows a concave or curved shape with the concavity following the isocontour of the magnetic field. Any depth or lateral extent may be provided, such as extending over at least 75% of the diameter of a bore of the PET detectors 16 and having a depth of 20-40 cm.

The material, shape, and size provide for annihilation of the positrons, resulting in gamma rays. The positrons interact with electrons, annihilating each other. The positron absorber 26 detects the beta emissions, resulting in gamma ray generation. All, many, or most inbound positrons eventually annihilate with an electron in the positron absorber 26, and the resulting annihilation radiation may be imaged by the PET camera. The gamma rays due to the annihilation may be detected by the PET detectors 16.

The positron absorber 26 is positioned outside of the bore of or beyond the extent or an end of the magnet 12. Any frame, fixed structure, robot, armature, or other arrangement may be used to position the positron absorber 26 relative to the magnet 12. The center of the positron absorber 26 is along a center axis of the bore of the magnetic 12 and/or the bore of the PET detectors 16, but may be offset from the center axis or axes. The positron absorber 26 is positioned in a region of the magnetic field where the magnetic field lines 27 passing through the object 20 diverge.

A surface of the positron absorber 26 closest to the sample 20 is any distance beyond the end of the magnet 12 and/or bore of the magnet 12, such as 20-80 cm. The further away, the greater the amount of divergence of the magnetic field lines 27. For example, the divergence of the magnetic field lines 27 is by at least 10% such that the spatial distribution of the beta emissions in the object 20 is detected in the positron absorber 26 with a greater lateral extent than in the object 20. In the example of FIG. 3, the positron absorber 26 is positioned from the end of the magnet 12 such that the magnetic field lines 27 diverge by about 100%. The density of the magnetic field lines 27 at the positron absorber 26 is half of the density of the magnetic field lines 27 within the bore of the magnet 12 and/or at the object 20.

The object 20 is placed in the higher field strength region. If the field strength, B, is sufficiently high relative to the mean energy of the emitted beta particles (e.g., a few Tesla/MeV), the beta particles are constrained to follow tight helical paths around the field lines 27 as they diverge. $Br^2$, where r is the gyro-radius, is an adiabatic invariant of motion. Thus, the gyro-radius increases as the distance between fields lines 27 increases. The 2D spatial distribution of beta particles reaching the surface of the positron absorber 26 correlates with the emission distribution at the object 20, but with a greater spread due to field line 27 divergence. The beta ray distribution at the positron absorber 26 is a magnified version of the emission distribution at the object 20. A detector with a given spatial resolution capability operated at the positron absorber 26 is thus be able to "see" the distribution of beta emissions at the object 20 with a higher resolution given a same detector density or resolution (i.e., magnetic lensing).

In the embodiment of FIG. 2, the positron absorber 26 and PET detectors 16 are replaced with a beta detector 28. Any beta detector 28 may be used, such as a plastic scintillator with an optical readout. The beta detector 28 may directly detect positrons, electrons, or both.

The beta detector 28 has a similar or same positioning as the positron absorber 26. The beta detector 28 is positioned to detect beta emissions after any amount of divergence of the magnetic field lines 27. This positioning provides for magnetic lensing.

In the embodiments of FIG. 1 or 2, the detection occurs on one side of the magnet 12. Since the beta emissions travel in either direction along the magnetic field lines 27, detectors (e.g., beta detector 28 or the combination of positron absorber 26 and PET detectors 16) may be positioned on either side or both sides of the magnet 12. Detectors on both sides may improve the efficiency of the beta emission imaging by combining detected beta emissions from both detectors.

In the embodiments of FIGS. 1 and 3, the PET portion is a PET system configured to detect annihilation events in the positron absorber 26. The PET system detects the rate or count of annihilation events.

The PET portion is shown as the PET detectors 16. Additional, different, or fewer components may be provided. Other parts of the PET portion may include data acquisition units (DAUs), power supplies, communications systems, image processing systems, tomography generation systems, and user interface systems. Any now known or later developed PET imaging system may be used. The location of the different components of the PET portion is within or outside the RF cabin, such as the image processing, tomography, power generation, and user interface components being outside the RF cabin. Power cables and fiber optic cables for communications connect the DAUs with the components outside the RF cabin through a filter plate.

The PET detectors 16 are crystals and photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used. Any gamma ray detector may be used.

The detectors 16 are arranged individually or in groups. A ring of detectors 16 in groups defines a field of view. The positron absorber 26 is positioned in this field of view or in the bore of the ring of detectors 16, so the ring of detectors 16 extends from or is entirely outside of the bore of the magnet 12. The ring has a cylinder shape that encompasses the bore or location for placement of the positron absorber 26 being scanned. For example, the PET detectors 16 have a 26 cm axial field of view centered in a region of the magnetic field with any amount of divergence from the bore of the magnet 12, such as at a position with at least divergence by 10% as compared to within the bore of the magnet 12. For the hybrid system 10 where the PET detectors 16 may be within the bore of the MR portion, the measurement configuration depicted in FIGS. 1 and 3 is achieved by pulling out the PET gantry of the hybrid system 10 to a service position. Fixed positioning or variable positioning of the PET detectors 16 relative to the magnet 12 may be provided.

The positron emission tomography system is configured to detect annihilation events in the positron absorber 26. The annihilation events from beta emissions from the object 20 are detected. The beta emissions travel from the object 20 and along the magnetic field lines 27 to the positron absorber 26 and interact with electrons in the positron absorber 26. The gamma rays resulting from the interaction are detected.

The detectors 16 generate three analog signals, two position signals and one energy signal. Each of the signals is output as a differential signal pair. Signals from the PET detectors 16 are directly digitized. Analog position and energy signals are filtered, amplified, and digitized inside the RF cabin, but may be digitized outside the RF cabin.

The PET portion, such as using the processor 22, is configured by software, hardware, and/or firmware to reconstruct a spatial distribution of the beta emissions in the object 20. The PET portion may reconstruct a three-dimensional distribution of annihilation events, providing a count for each voxel or location in three-dimensions within the positron absorber 26. The counts along the field lines may be summed, averaged, or combined to provide a count for each field line or pixel in a two-dimensional distribution. Alternatively, the counts at a given depth in the positron absorber 26 are used. Since the beta emissions travel along the field lines from any depth in the object 20, the beta emissions represent a two-dimensional distribution of emissions. A count from the positron absorber 26 for each field line or pixel provides the two-dimensional distribution from the object 20. The spatial distribution extends over two dimensions orthogonal to the center axis of the bore of the magnet 20, the field lines 27, and/or a direction of travel of the beta particles. The density or resolution of the spatial distribution at the positron absorber 26 is different than the density or resolution at the object 20 due to divergence of the field lines 27, but the same spatial distribution is represented.

To find the two-dimensional spatial distribution, the PET system reconstructs the detected annihilation events into a spatial representation. The detections along the various lines of response or detector pairs are tomographically reconstructed to determine the likely locations at which annihilation events occurred. Any reconstruction may be used, such as filtered back projection, maximum likelihood-expectation maximization, or ordered subsets expectation maximization. The reconstruction provides an annihilation rate per spatial location over a given period.

The processor 22 is a computer, controller, server, application specific integrated circuit, field programmable gate array, graphics processing unit, digital circuit, analog circuit, or combinations thereof. In one embodiment, the processor 22 is a computer that is part of the PET system, but a separate component may be used. The processor 22 reconstructs the received PET signals. Due to the magnetic field lines 27, a greater portion of the beta emissions are directed to the positron absorber 26 or detector 28. This allows for greater counts than without the magnetic field, resulting in a higher sensitivity.

The PET signals at a given depth, at a surface, combined along magnetic lines 27, or other locations represent the two-dimensional distribution of emissions from the object 20. For example, a map of the $B_0$ magnetic field gives the relation or spatial transform between mean detection in the positron absorber 26 and emission points from the object 20. The mean of the detected PET signals along each magnetic field line in a two-dimensional pattern at the resolution of the detector provides a representation of the two-dimensional distribution of beta emissions of the object 20. The map of the magnetic field is empirically calibrated, but may be modeled. A magnetometer or measurements with point sources at known positions may be used to determine the magnetic field and corresponding spatial transform due to divergence.

In the example of FIG. 3, the divergence of the magnetic field lines 27 from the object 20 to the positron absorber provides a 2× geometrical gain. The detection by the PET portion at one resolution represents the beta emissions at times two resolution due to divergence.

An additional gain in resolution may be realized as a consequence of the helical motion of the beta particles around the B field lines caused by the Lorentz force. An increase in the magnetic field results in tighter helical motion about the magnetic field lines of the beta particles, so increased magnetic field provides increased resolution. Any decrease in spatial accuracy due to the helical motion is reduced.

In one example, $^{68}$Ga is used in the radio-tracer. $^{68}$Ga emits positrons with a maximum energy $E_{max}$=1.9 MeV and a mean energy of about 830 keV. The object 20 is positioned at a uniform 3T region of an MR system. For a 3 mm diameter source, an imaged full width half maximum (FWHM) beam diameter of 5-6 mm is maintained over a factor of $10^3$ attenuation. The range of such a beam is 0.52 g/cm², or over 4 meters in air. For a small source (e.g., 0.2 mm), the intrinsic beam FWHM for $^{68}$Ga rises from 1.7 mm initially to 3.8 mm at the end of range. The intrinsic beam width decreases as B increases approximately as $B^{-0.9}$. In a 9T field, the diameter remains in the range 0.6-1.5 mm. In a 3T field, the beam diameters for lower energy positron emitters, such as $^{18}$F and $^{11}$C, are significantly smaller, resulting in greater resolution due to smaller gyroscopic radii. The lower energy emitters may not penetrate as far.

Using the PET signals, the attenuation of the beta rays in the positron absorber 26 may be estimated. The processor 22 determines the total positron flux entering a point on the surface of, or at any depth within, the positron absorber 26 from the reconstructed PET signals. Any now known or later developed positron attenuation tomography (PAT) technique is used. A magnetically constrained $\beta_+$-ray beam may maintain spatial coherence over three orders of magnitude attenuation in matter while signaling intensity via the generated annihilation radiation. With the divergence of the beam or beta emissions magnetically constrained, the PET camera detects the attenuation of the positron beam along the magnetic field lines 27 within the positron absorber 26 due to positron-electron annihilations. The resulting annihilation distribution is tomographically imaged by the PET camera. If all positrons are stopped within the absorber, this image may be converted into a map of the positron beam's flux distribution without auxiliary measurements.

The attenuation of $\beta_+$-rays in matter is a complex process involving inelastic electron scattering, elastic nuclear scattering, the formation of positronium, and ultimately, positron-electron annihilation. When a ~1 MeV $\beta^+$-decay source (e.g., $^{68}$Ga) is exposed within the field of the magnet 12, the emitted positrons follow helical paths around the field lines with gyroradii on the order of 1 mm due to the action of the Lorentz force. As a result, a non-diverging positron beam is formed parallel to the magnetic field lines across the PET's field of view. Losses in air are modest (~1%/cm) and thus a vacuum system is not required for beam transport. The PET portion may accurately image the annihilation rate along the beam within the positron absorber 26 by detecting the generated annihilation radiation.

The processor 22 is configured to determine the positron attenuation or flux within the absorber 26. The PET detectors 16 detect annihilation per unit time along lines of response. Upon reconstruction, a count or annihilation rate per voxel is provided. This annihilation rate may be understood as the product of the positron flux and the linear attenuation coefficient of the material of the positron absorber 26 at that point. Since the only loss mechanism of positrons from the beam is annihilation with an electron, if the beam is fully stopped within the field of view of the PET detectors 16, the positron flux at any point may be estimated from the integral of annihilation rate down-beam (i.e., along the magnetic field line 27) from that point. This allows the flux and positron attenuation components of the annihilation rate image to be distinguished, providing for positron attenuation tomography. The positron attenuation is determined by calculation using emissions measured by the positron emission tomography system in response to the transmitted beams of positrons from the object 20 into the positron absorber 26. The spatial distribution of the annihilation events along the beams in the positron absorber 26 is used by the processor 22 to estimate the positron flux along the beams in the positron absorber 26.

The positron flux is estimated as a scalar value or as a curve of flux as a function of depth along the magnetic field lines. The energy or amount of radiation transmitted from the object 20 does not need to be known. By having the beams terminate in the positron absorber 26, the integration of rate of annihilation along the beam may be used to estimate the positron flux at different locations.

The flux passing through each of the locations in the object along the positron beams is equal to the flux passing through a previous, up-beam location minus the annihilation event rate between the two locations. Where the positron beam terminates in the object, the flux may be estimated for the different locations in the object along or prior to the termination of the positron beam from the sum of all the annihilations along the positron beam between the location and the termination point. The processor 22 determines the positron flux by an integration of the annihilations along the beams within the positron absorber 26.

The processor 22 is configured to correct for absorption of the beta emissions in the object 20 based on the positron flux measured in the absorber 26. For example, where the object 20 is a leaf, a stem or other denser or thicker structure may attenuate beta emissions generated in the leaf and passing through on the way to the positron absorber 26. Such self-absorption is a confounding effect in beta emission imaging. As magnetically constrained positron beams pass through matter, their energy is degraded, causing their linear attenuation coefficients (LACs) to increase. This increase is systematic, depending mainly on the amount of material the beam has passed through. This non-exponential attenuation may be observed with PAT, and used to correct for differences in the total attenuation experienced by the beam between one point in the image and another, such as might be caused by variation in sample thickness. The positron absorber 26 is chosen to be of uniform composition and density. Due to the variation of the LACs with attenuation, the curve of flux versus depth has a characteristic shape that depends mainly on the amount of attenuation the positrons have experienced. The more attenuation the positrons have experienced in the object 20 before entering the stopper 26, the more this characteristic shape will be shifted toward the front surface of the stopper (toward the object). The relative attenuation of the positrons in the object 20 along each magnetic field line may thus be determined from the relative shifts of the flux curves in the stopper 26 along these lines. The relative attenuation in the object 20 between two points in the image is equal to the relative attenuation of the beam in the stopper 26 over this depth shift. The correction of the beta emission image for self-absorption along a given field line is therefore proportional to the difference in counts at the surface of the stopper 26 between the shifted and unshifted flux curves.

Figure 4:
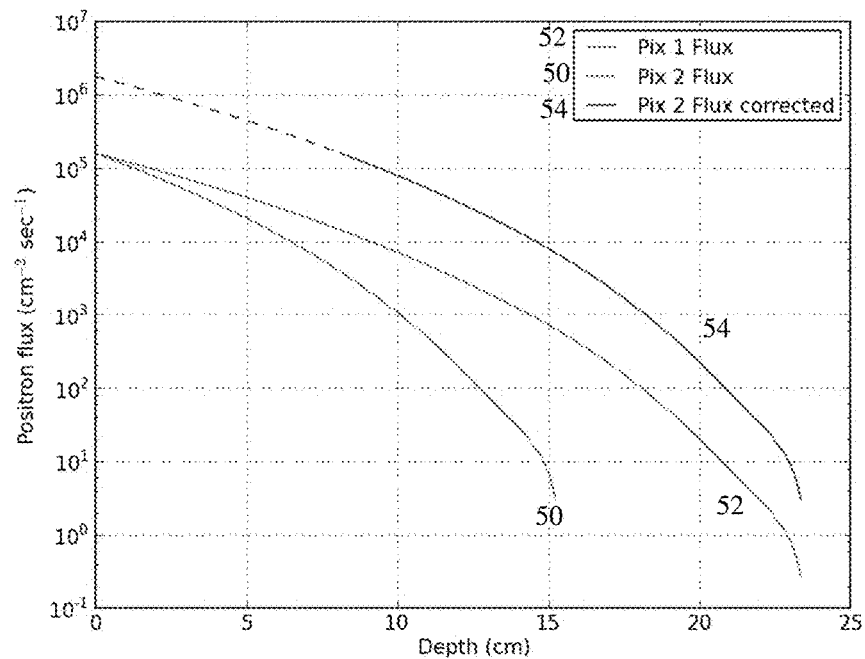
FIG. 4 shows positron flux as a function of depth for beta imaging correction based on detected positron attenuation.

The processor 22 is configured to correct for each entry point of the beta emissions into the positron absorber 26 based on the rate of positron flux decrease as a function of depth within the positron absorber 26. The attenuation is used to correct the scalar value representing the count of beta emissions for each location in the two-dimensional spatial distribution of emissions. FIG. 4 shows the positron flux based on PAT for two pixels, field lines 27, and/or beta emission beams from the object 20 in the positron absorber 26. The curve 52 is the positron flux entering the positron absorber 26 at pixel 1 versus depth within the positron absorber 26. The flux is estimated from measured data in PAT. The curve 50 is a flux distribution for a second pixel that has the same apparent entry flux. However, the beam at this point has lower energy as a consequence of having passed through more material (e.g., self-absorption), and thus exhibits a greater attenuation rate. If the depth of the curve 50 is adjusted until its attenuation profile matches the curve 52, the curve 54 results. Any matching may be used. For example, the curve 50 is translated in depth to best match the curve 52. The translation at which the curvature is most similar is the one at which the total attenuation should be similar. Translating in depth emulates finding an initial or entry flux that results in the measured rate of attenuation. The translation results in the entry flux at the 0 depth point being greater. This greater flux value, when assigned to pixel 2, compensates the greater attenuation in the positrons entering pixel 2 experienced in the object 20.

The reference curve (e.g., curve 52) is from a selected field line, such as for a positron beam known not to have or to have minimal self-absorption. Alternatively, an average curve from all the measured curves is used. A modeled curve may be used.

Once the matching is performed, the resulting curve 54 does not cross the zero depth. The curve 54 is extrapolated using the shape of curve 52 to determine the intersection with the zero depth. This extrapolation is shown in FIG. 4 as the dashed part of the curve 54. The extrapolation indicates that the flux at pixel 2 would be 10× greater if corrected for self-attenuation in the object 20 of the same amount experienced at pixel 1 or the reference curve 52.

The zero-depth crossing flux is used as the scalar value or a relative weight for adjusting the count for the pixel or positron beam. The counts may be relatively weighted to correct for self-absorption, which varies across the pixels or beams. This potentially reduces the effects of variations in emission efficiency across the object 20.

The processor 22 is configured to generate an image of the beta emissions from the object 20. The image is a cross-section or projection, providing a two-dimensional distribution of emissions from the three-dimensional object 20. The PAT, flux, or PET signals are mapped to intensity, color, or another image information. The image represents the spatial distribution of the beta emissions.

The display 23 is a device, such as a CRT, LCD, plasma screen, projector, printer, or other display device. The display 23 outputs information to the user, such as an image showing uptake or function of the object 20. The display 23 is configured to create the output by the processor 22 storing an image or information in a display plane buffer.

The display 23 provides an image of the one or two-dimensional spatial distribution of the beta emissions. Where the radio-isotope gathers or attaches in the object 20, a greater emission count results. These regions are indicated by greater intensity or by color in the image. A beta emission image of the two-dimensional distribution in the object 20 is displayed.

FIG. 5 shows one embodiment of a method for beta emission imaging. For beta emission imaging, electrons or positrons emitted due to decay are imaged. The beta emission imaging uses magnetic lensing and/or correction of self-absorption.

The method is implemented using the system 10 of FIG. 1, the system of FIG. 2, a computer, and/or other devices. For example, a magnet and radio-isotope are used for act 60; a PET detector, beta camera, or direct beta detector perform act 62; and a processor (e.g., computer of a PET system, MR system, or workstation) performs acts 64-68.

The method is performed in the order shown, but other orders may be used. Additional, different, or fewer acts may be provided. For example, act 68 is not performed. In another example, acts 64 and/or 66 are not performed where magnetic lensing is used without correction for self-absorption. In yet another example, act 62 is performed without relying on divergence of the magnetic field lines (i.e., detection is performed in the uniform region of the magnetic field such as in the bore of the magnet or MR system) for correction for self-absorption without magnetic lensing.

In act 60, the radio-isotope generates beta emissions. The radio-isotope is ingested, injected, or otherwise placed within a sample, such as plant or animal tissue sample (e.g., biological object). The radio-isotope is tagged or connected with a molecule or molecules that attach to or respond to functional processes in the tissue sample, so greater numbers of the radio-isotope are at locations associated with the functional process. Due to decay, the radio-isotopes generate beta emissions. Beta emissions are generated more frequently or in greater numbers at the locations for the functional process.

The sample is positioned in a magnetic field. For example, the sample is positioned in a bore of a cylindrical magnet. The magnetic field lines at the sample have a given density. Once positioned, the beta emissions may be used to image. Due to the magnetic field, positrons or electrons are directed along magnetic field lines to a detector or stopper. For example, the beta emissions travel out of the bore to a detector or stopper.

In act 62, a detector detects values for a spatial distribution of beta emissions from the biological object or sample. The values are counts of the beta emissions. For each pixel of the detector or at the resolution for detection, a number of beta emissions is counted. Any beta emissions detection may be used.

For self-absorption correction without magnetic lensing, the detector is within the bore or at a location where the magnetic field lines have a same or similar (e.g., within 5%) density as the sample. For magnetic lensing, the detector detects the beta emissions at a location spaced from the sample where the magnetic field lines have a different density than at the sample. For example, the detector is about 30-70 cm beyond an end of a bore of a main field magnet of an MR system. Greater or lesser distance may be used. By being positioned beyond an end of the bore along the magnetic field lines, the magnetic field lines diverge. The spatial distribution of counts may be detected with a lower resolution detector than for the denser magnetic field lines at the sample. Due to the lesser field line density beyond the bore and the beta emissions being constrained to the magnetic field, the detector may detect a magnified version of the beta emissions. For example, a detector with 1 mm per cell resolution may detect beta emissions of the sample at 0.5 mm per cell due to the divergence of the magnetic field lines by 100%.

The detector is positioned to intercept all or some of the magnetic field lines that pass through the sample. A beta detector may directly detect the beta emissions, providing a count for each detectable location. The beta detector intercepts the beta emissions at the density corresponding to the magnetic field lines at the position of the detector.

In another embodiment for detecting positrons, the detector is a stopper. For example, a foam block of uniform material is positioned at the location spaced from the bore of the magnet. The beta emissions annihilate within the stopper, generating gamma rays. At any given location in the stopper prior to termination of the beam, some of the positrons interact with electrons, resulting an in an annihilation. Each annihilation generates a pair of gamma rays traveling in generally opposite directions.

The annihilation rate of the positrons in the stopper is detected by a ring of photon detectors or other PET detectors positioned at least partly around the stopper. The detectors detect the gamma rays. Relative timing is used to pair gamma rays, defining an event along a line of response. The events and lines of response may be used to determine the locations of the annihilations within the stopper. After tomographic reconstruction, a count or annihilation rate for each voxel or location in the stopper is provided.

The count at a surface of the stopper, at a given depth within the stopper or along the magnetic field lines, or from a combination of voxels along the beta emission beams (i.e., along different magnetic field lines) is determined. This distribution of counts provides the spatial distribution in two dimensions of the beta emissions. Due to magnetic lensing, the spatial distribution is of the sample at a higher resolution than the actual detection.

For self-absorption correction, the processor or PET system estimates the positron attenuation effect in the object 20 from the spatial distribution of the positron flux in the stopper 26 in act 64. The flux along each magnetic field line or pixel within the stopper is determined. The flux of the beta emissions in the stopper spaced from the biological object or sample is calculated. The flux is estimated for some or all of a plurality of locations through which the positrons pass before termination. The flux is estimated directionally along the magnetic field lines. The magnetic field causes the positrons to pass into the stopper, so the flux in that stopper for the locations along the positron beam is estimated. Different fluxes may be estimated for different locations.

Alternatively, the self-absorption correction for the object 20 may be based on an estimate of the apparent attenuation coefficients of the positron beams in the stopper 26, as given by the PAT transformation. The attenuation coefficients are numerically equal to the (negative of the) logarithmic derivative of the flux curve.

In act 66, the PET system or processor corrects the counts for each spatial location. The correction is for self-absorption. The estimated positron flux in the stopper 26 is used to correct the counts. A magnitude of attenuation is found by comparing the flux curve to a reference flux curve. The comparison shifts the curve in depth to determine an amount of attenuation of the positron beam in the sample. The shifted flux curve, when extrapolated to (or truncated at) the surface of the stopper 26 indicates the flux that would have been measured in that spatial location had there been no difference in self-absorption in the object 20 compared to the reference curve. This constitutes a correction of the flux for that location. The flux represents the beta emissions, so correction of the flux corrects the values of the beta emissions detected for the location.

In act 68, the PET system or processor forms a beta emission image. The two-dimensional spatial distribution of beta emissions is mapped to display values. The flux, counts, directly detected beta emissions, PAT values, or other representation of the intensity of emissions from different locations are displayed. The image represents the spatial distribution of the beta emissions from the biological object. The effects of efficiency variation are reduced due to the correction for self-absorption. The resolution relative to the object being imaged is greater due to the magnetic lensing.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for magnetic lensing in beta emission imaging, the method comprising:
generating beta emissions from a sample positioned in magnetic field lines having a first density;
detecting the beta emissions at a location spaced from the sample where the magnetic field lines have a second density, less than the first density; and
forming an image of the detected beta emissions of the sample,
wherein the beta emissions comprise positrons, and wherein detecting comprises detecting annihilation events of the positrons interacting with a stopper at the location with a detector ring for positron emission tomography, the stopper being within the detector ring.

2. The method of claim 1 wherein generating comprises generating the beta emissions with the sample positioned in a bore of a cylindrical magnet.

3. The method of claim 1 wherein detecting comprises detecting with a beta detector positioned where the magnetic field lines have diverged from the first density to the second density, the beta detector intercepting the magnetic field lines at the second density.

4. The method of claim 1 wherein detecting comprises detecting a spatial distribution of counts of the positrons.

5. The method of claim 1 further comprising:
estimating positron attenuations of the positrons in the spatial distribution; and
correcting the counts as a function of the positron attenuations.

6. The method of claim 1 wherein detecting where the magnetic field lines have the second density comprises detecting a magnified version of the beta emissions at the first density due to divergence of the magnetic field lines from the first density to the second density.

7. A method for magnetic lensing in beta emission imaging, the method comprising:
generating beta emissions from a sample positioned in magnetic field lines having a first density;
detecting the beta emissions at a location spaced from the sample where the magnetic field lines have a second density, less than the first density; and
forming an image of the detected beta emissions of the sample,
wherein detecting where the magnetic field lines have the second density comprises detecting a magnified version of the beta emissions at the first density due to divergence of the magnetic field lines from the first density to the second density.

* * * * *